(12) United States Patent  (10) Patent No.: US 7,723,371 B2
Walter et al.  (45) Date of Patent: May 25, 2010

(54) MICROBIOCIDES

(75) Inventors: Harald Walter, Stein (CH); Camilla Corsi, Stein (CH); Josef Ehrenfreund, Allschwil (CH); Hans Tobler, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 12/092,338

(22) PCT Filed: Nov. 13, 2006

(86) PCT No.: PCT/EP2006/010865

§ 371 (c)(1),
(2), (4) Date: Aug. 20, 2008

(87) PCT Pub. No.: WO2007/057139

PCT Pub. Date: May 24, 2007

(65) Prior Publication Data

US 2009/0054496 A1  Feb. 26, 2009

(30) Foreign Application Priority Data

Nov. 15, 2005 (EP) .................................. 05024968

(51) Int. Cl.
A01N 43/56 (2006.01)
(52) U.S. Cl. .................. 514/406; 514/355; 514/423; 514/365; 548/374.1; 548/537; 548/255; 546/316
(58) Field of Classification Search .................. 514/355, 514/406, 423, 365; 548/374.1, 537, 255; 546/316
See application file for complete search history.

(56) References Cited

U.S. PATENT DOCUMENTS 6,087,542 A  7/2000  Eicken et al.

2003/0004053 A1  1/2003  Soloveichik et al.

FOREIGN PATENT DOCUMENTS

| WO | 03074491 | 9/2003 |
|---|---|---|
| WO | 2004035589 | 4/2004 |
| WO | 2004039799 | 5/2004 |

*Primary Examiner*—Kamal A Saeed
*Assistant Examiner*—Valerie Rodriguez-Garcia
(74) *Attorney, Agent, or Firm*—James Cueva

(57) ABSTRACT

The invention relates to a fungicidally active compound of the general Formula (I): where Het is a 5- or 6-membered heterocyclic ring containing one to three heteroatoms, each independently selected from oxygen, nitrogen and sulphur, the ring being substituted by the groups $R^3$, $R^4$ and $R^5$; $R^1$ and $R^2$ are independently H, halo, $C_{1-4}$ alkyl or $C_{1-4}$ haloalkyl; and $R^3$, $R^4$ and $R^5$ are each, independently, H, halo, $C_{1-4}$ alkyl, $C_{1-4}$ haloalkyl or $C_{1-4}$ haloalkoxy, provided that at least one of $R^3$, $R^4$ and $R^5$ is not H; to the preparation of these compounds, to novel intermediates used in their preparation, to agrochemical compositions which comprise at least one of the novel compounds as an active ingredient, to the preparation of the compositions and to the use of the active ingredients or compositions in agriculture or horticulture for controlling or preventing infestations of plants by phytopathogenic microorganisms, especially fungi.

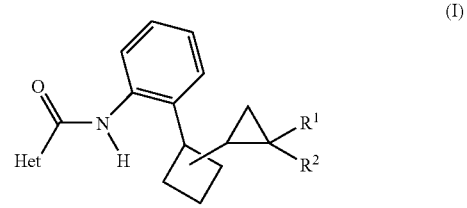

(I)

16 Claims, No Drawings

MICROBIOCIDES

The present invention relates to novel carboxamides derived from novel ortho-substituted anilines. The carboxamides have microbiocidal activity, in particular fungicidal activity. The invention also relates to the preparation of these compounds, to the novel ortho-substituted aniline intermediates used in the preparation of the compounds, to agrochemical compositions which comprise at least one of the novel carboxamides as an active ingredient, to the preparation of the compositions and to the use of the active ingredients or compositions in agriculture or horticulture for controlling or preventing infestation of plants by phytopathogenic microorganisms, especially fungi.

Various carboxamides and their use as microbiocides are described in the literature, for example in WO 03/074491 and WO 04/035589. The present invention is concerned with the provision of alternative carboxamides having microbiocidal activity.

The present invention provides a compound of the general formula (I):

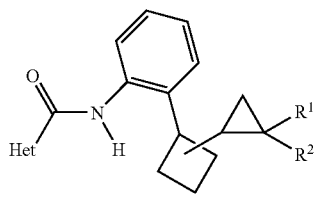

wherein Het is a 5- or 6-membered heterocyclic ring containing one to three heteroatoms, each independently selected from oxygen, nitrogen and sulphur, the ring being substituted by the groups $R^3$, $R^4$ and $R^5$;
$R^1$ and $R^2$ are independently H, halo, $C_{1-4}$ alkyl or $C_{1-4}$ haloalkyl; and
$R^3$, $R^4$ and $R^5$ are each, independently, H, halo, $C_{1-4}$ alkyl, $C_{1-4}$ haloalkyl or $C_{1-4}$ haloalkoxy, provided that at least one of $R^3$, $R^4$ and $R^5$ is not H.

The cyclopropyl ring may be attached to the cyclobutyl ring at either its 2- or 3-position, the anilide moiety being attached to the 1-position of the cyclobutyl ring.

Het may be any 5- or 6-membered heterocyclic ring containing one to three oxygen, nitrogen or sulphur heteroatoms. Compounds of particular interest are those where Het is pyrrolyl, pyrazolyl, thiazolyl, oxazolyl, imidazolyl, triazolyl, pyridyl, pyrimidinyl, pyridazinyl, 2,3-dihydro-[1,4]oxathiinyl, oxazinyl, thiazinyl or triazinyl. The heterocyclic ring contains at least one substituent, which is one of the groups $R^3$, $R^4$ and $R^5$ with a value other than H. Typical values of the groups $R^3$, $R^4$ and $R^5$ are H, fluoro, chloro, bromo, methyl, ethyl, trifluoromethyl, difluoromethyl and monofluoromethyl.

$R^1$ and $R^2$ are independently H, halo, $C_{1-4}$ alkyl or $C_{1-4}$ haloalkyl. Normally they will be the same. Typically, they are both H or both $C_{1-4}$ alkyl, and usually both H or both methyl.

Halo, either as a lone substituent or in combination with another substituent (e.g. haloalkyl) is generally fluoro, chloro, bromo or iodo, usually fluoro, chloro or bromo, and especially fluoro or chloro.

Each alkyl group (or alkyl moiety of haloalkyl) is a straight or branched chain containing from 1 to 4 carbon atoms, and is methyl, ethyl, n-propyl, n-butyl, iso-propyl, sec-butyl, iso-butyl or t-butyl. Typically it is methyl or ethyl.

Haloalkyl moieties are alkyl moieties which are substituted by one or more of the same or different halogen atoms and are, for example, monofluoromethyl, difluoromethyl, trifluoromethyl, monochloromethyl, dichloromethyl, trichloromethyl, 2,2,2-trifluoroethyl, 2,2-difluoroethyl, 2-fluoroethyl, 1,1-difluoroethyl, 1-fluoroethyl, 2-chloroethyl, pentafluoroethyl, 1,1-difluoro-2,2,2-trichloroethyl, 2,2,3,3-tetrafluoroethyl, 2,2,2-trichloroethyl, difluorochloromethyl and dichlorofluoromethyl, and typically, monofluoromethyl, difluoromethyl and trifluoromethyl.

The compounds of formula (I) may exist as different geometric or optical isomers or in different tautomeric forms. These may be separated and isolated by well-known (usually chromatographic) techniques, and all such isomers and tautomers and mixtures thereof in all proportions as well as isotopic forms, such as deuterated compounds, are part of the present invention. In particular, cis-trans isomerism exists because of the presence of different substituents on different carbon atoms of the cyclobutane ring. The present invention includes both cis and trans isomers of novel compounds where such isomerism exists, both separately and as mixtures in any proportions. Usually, the compound of formula (I) and the novel intermediates (II) and (III), described later, will be obtained as a cis/trans mixture when the cyclopropyl ring is attached to the 3-position of the cyclobutyl ring and, predominantly, as the cis isomer when the cyclopropyl ring is attached to the 2-position of the cyclobutyl ring.

In one aspect of the present invention, Het, $R^3$, $R^4$ and $R^5$ are as defined above and $R^1$ and $R^2$ are both H or both $C_{1-4}$ alkyl. Usually, they are both H or both methyl. The cyclopropyl ring is attached to either the 2- or 3-position of the cyclobutyl ring.

In another aspect of the invention, $R^1$ and $R^2$ are as defined above and Het is pyrrolyl, pyrazolyl, thiazolyl, oxazolyl, imidazolyl, triazolyl, pyridyl, pyrimidinyl, pyridazinyl, 2,3-dihydro-[1,4]oxathiinyl, oxazinyl, thiazinyl or triazinyl, the rings being substituted by at least one of the groups $R^3$, $R^4$ and $R^5$ as defined above. The cyclopropyl ring is attached to either the 2- or 3-position of the cyclobutyl ring.

Usually Het is pyrrolyl (especially pyrrol-3-yl), pyrazolyl (especially pyrazol-4-yl), thiazolyl (especially thiazol-5-yl), oxazolyl (especially oxazol-5-yl), 1,2,3 triazolyl (especially 2-H-1,2,3-triazolyl), pyridyl (especially pyrid-3-yl) or 2,3-dihydro-[1,4]oxathiinyl (especially 2,3-dihydro-[1,4]oxathiin-5-yl). Typically it is pyrrol-3-yl, pyrazol-4-yl, thiazol-5-yl or pyrid-3-yl and preferably pyrazol-4-yl.

The substituents of Het ($R^3$, $R^4$ and $R^5$), which are independent of each other, are usually H, fluoro, chloro, bromo, $C_{1-4}$ alkyl (especially methyl and ethyl) or $C_{1-4}$ haloalkyl (especially trifluoromethyl, difluoromethyl, monofluoromethyl and chlorodifluoromethyl).

Typical values of Het are the pyrrol-3-yl of the general formula (Het$^1$) and the pyrazol-4-yl of the general formula (Het$^2$):

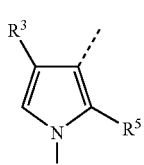
(Het¹)

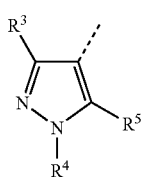
(Het²)

wherein R³ is $C_{1-4}$ alkyl or $C_{1-4}$ haloalkyl (especially methyl, trifluoromethyl, difluoromethyl or monofluoromethyl) R⁴ is $C_{1-4}$ alkyl (especially methyl or ethyl), and R⁵ is H or halo (especially H, fluoro or chloro); the thiazol-5-yl and oxazol-5-yl of the general formula (Het³):

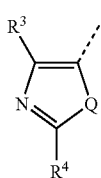
(Het³)

wherein Q is oxygen or sulphur, R³ is $C_{1-4}$ alkyl or $C_{1-4}$ haloalkyl (especially methyl, trifluoromethyl or difluoromethyl) and R⁴ is $C_{1-4}$ alkyl (especially methyl or ethyl); the 2H-1,2,3-triazol-4-yl of the general formula (Het⁴):

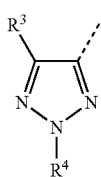
(Het⁴)

wherein R³ is $C_{1-4}$ alkyl or $C_{1-4}$ haloalkyl (especially methyl, trifluoromethyl, difluoromethyl or monfluoromethyl) and R⁴ is $C_{1-4}$ alkyl (especially methyl or ethyl); the pyrid-3-yl of the general formula (Het⁵):

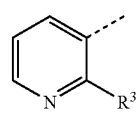
(Het⁵)

wherein R³ is halo or $C_{1-4}$ haloalkyl (especially chloro, bromo or trifluoromethyl); or the 2,3-dihydro[1,4]oxathiin-5-yl of the general formula (Het⁶):

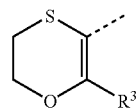
(Het⁶)

wherein R³ is $C_{1-4}$ alkyl or $C_{1-4}$ haloalkyl (especially methyl or trifluoromethyl). Compounds of particular interest are those where Het has one of the typical values described immediately above and R¹ and R² are both H or both methyl.

In another aspect of the present invention there is provided a compound of the general formula (I) wherein Het is pyrrol-3-yl substituted at the 1-position by $C_{1-4}$ alkyl (especially methyl or ethyl), substituted at the 4-position by $C_{1-4}$ alkyl or $C_{1-4}$ haloalkyl (especially methyl, trifluoromethyl, difluoromethyl or monofluoromethyl) and optionally substituted at the 2-position by halo (especially fluoro or chloro); pyrazolyl-4-yl substituted at the 1-position by $C_{1-4}$ alkyl (especially methyl or ethyl), substituted at 3-position by $C_{1-4}$ alkyl or $C_{1-4}$ haloalkyl (especially methyl, trifluoromethyl, difluoromethyl or monofluoromethyl) and optionally substituted at the 5-position by halo (especially fluoro or chloro); thiazol-5-yl or oxazol-5-yl (usually thiazol-5-yl) substituted at the 2-position by $C_{1-4}$ alkyl (especially methyl or ethyl) and substituted at the 4-position by $C_{1-4}$ alkyl or $C_{1-4}$ haloalkyl (especially methyl, trifluoromethyl or difluoromethyl); 2,3-dihydro[1,4]oxathiin-5-yl substituted at the 6-position by $C_{1-4}$ alkyl or $C_{1-4}$ haloalkyl (especially methyl or trifluoromethyl); pyrid-3-yl substituted at the 2-position by halo or $C_{1-4}$ haloalkyl (especially chloro, bromo or trifluoromethyl); or 2H-1,2,3-triazol-4-yl substituted at the 2-position by $C_{1-4}$ alkyl (especially methyl or ethyl) and at the 5-position by $C_{1-4}$ alkyl or $C_{1-4}$ haloalkyl (especially methyl, trifluoromethyl, difluoromethyl or monofluoromethyl); and R¹ and R² are both H or both $C_{1-4}$ alkyl (especially methyl). The cyclopropyl ring is attached to either the 2- or 3-position of the cyclobutyl ring.

In yet another aspect of the present invention there is provided a compound of the general formula (I) wherein Het is 2-$C_{1-4}$ alkyl-4-$C_{1-4}$ haloalkylthiazol-5-yl, 2-halopyrid-3-yl, 1-$C_{1-4}$ alkyl-4-$C_{1-4}$ haloalkylpyrrol-3-yl or 1-$C_{1-4}$ alkyl-3-$C_{1-4}$ haloalkylpyrazol-4-yl; R¹ and R² are both hydrogen; and the cyclopropyl ring is attached to either the 2- or 3-position of the cyclobutyl ring.

In still yet another aspect of the present invention there is provided a compound of the general formula (I) wherein Het is 2-methyl-4-trifluoromethylthiazol-5-yl, 2-chloro-pyrid-3-yl, 1-methyl-4-trifluoromethylpyrrol-3-yl, 1-methyl-3-trifluoromethylpyrazol-4-yl or 1-methyl-3-difluoromethylpyrazol-4-yl; R¹ and R² are both H; and the cyclopropyl ring is attached to either the 2- or 3-position of the cyclobutyl ring.

The invention is further illustrated by the individual compounds of formula (I) listed below in Tables 1 to 12. Characterising data is given in Table 13.

TABLE 1

Compounds of formula (IA)

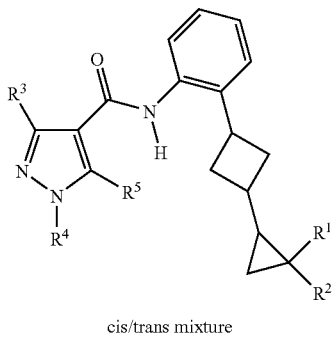

cis/trans mixture

| Compound Number | R$^1$ | R$^2$ | R$^3$ | R$^4$ | R$^5$ |
|---|---|---|---|---|---|
| 1.1 | H | H | CF$_3$ | CH$_3$ | H |
| 1.2 | H | H | CF$_2$H | CH$_3$ | H |
| 1.3 | H | H | CFH$_2$ | CH$_3$ | H |
| 1.4 | H | H | CH$_3$ | CH$_3$ | F |
| 1.5 | H | H | CH$_3$ | CH$_3$ | Cl |
| 1.6 | H | H | CF$_3$ | C$_2$H$_5$ | H |
| 1.7 | H | H | CF$_2$H | C$_2$H$_5$ | H |
| 1.8 | H | H | CFH$_2$ | C$_2$H$_5$ | H |
| 1.9 | H | H | CH$_3$ | C$_2$H$_5$ | F |
| 1.10 | H | H | CH$_3$ | C$_2$H$_5$ | Cl |
| 1.11 | CH$_3$ | CH$_3$ | CF$_3$ | CH$_3$ | H |
| 1.12 | CH$_3$ | CH$_3$ | CF$_2$H | CH$_3$ | H |

TABLE 2

Compounds of formula (IB)

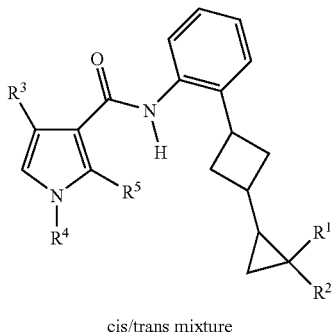

cis/trans mixture

| Compound Number | R$^1$ | R$^2$ | R$^3$ | R$^4$ | R$^5$ |
|---|---|---|---|---|---|
| 2.1 | H | H | CF$_3$ | CH$_3$ | H |
| 2.2 | H | H | CF$_2$H | CH$_3$ | H |
| 2.3 | H | H | CFH$_2$ | CH$_3$ | H |
| 2.4 | H | H | CH$_3$ | CH$_3$ | F |
| 2.5 | H | H | CH$_3$ | CH$_3$ | Cl |
| 2.6 | H | H | CF$_3$ | C$_2$H$_5$ | H |
| 2.7 | H | H | CF$_2$H | C$_2$H$_5$ | H |
| 2.8 | H | H | CFH$_2$ | C$_2$H$_5$ | H |
| 2.9 | H | H | CH$_3$ | C$_2$H$_5$ | F |
| 2.10 | H | H | CH$_3$ | C$_2$H$_5$ | Cl |
| 2.11 | CH$_3$ | CH$_3$ | CF$_3$ | CH$_3$ | H |
| 2.12 | CH$_3$ | CH$_3$ | CF$_2$H | CH$_3$ | H |

TABLE 3

Compounds of Formula (IC)

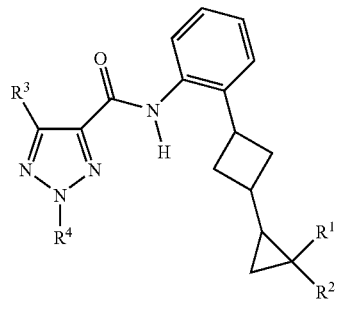

cis/trans mixture

| Compound Number | R$^1$ | R$^2$ | R$^3$ | R$^4$ |
|---|---|---|---|---|
| 3.1 | H | H | CF$_3$ | CH$_3$ |
| 3.2 | H | H | CF$_2$H | CH$_3$ |
| 3.3 | H | H | CFH$_2$ | CH$_3$ |
| 3.4 | H | H | CH$_3$ | CH$_3$ |
| 3.5 | H | H | CF$_3$ | Et |
| 3.6 | H | H | CF$_2$H | Et |
| 3.7 | H | H | CFH$_2$ | Et |
| 3.8 | H | H | CH$_3$ | Et |
| 3.9 | CH$_3$ | CH$_3$ | CF$_3$ | CH$_3$ |
| 3.10 | CH$_3$ | CH$_3$ | CF$_2$H | CH$_3$ |

TABLE 4

Compounds of formula (ID)

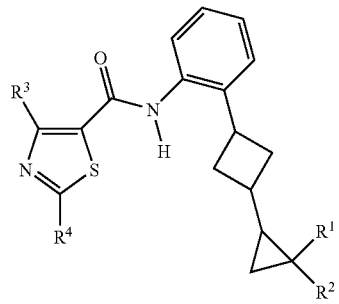

cis/trans mixture

| Compound Number | R$^1$ | R$^2$ | R$^3$ | R$^4$ |
|---|---|---|---|---|
| 4.1 | H | H | CF$_3$ | CH$_3$ |
| 4.2 | H | H | CF$_2$H | CH$_3$ |
| 4.3 | H | H | CH$_3$ | CH$_3$ |
| 4.4 | H | H | CF$_3$ | C$_2$H$_5$ |
| 4.5 | H | H | CF$_2$H | C$_2$H$_5$ |
| 4.6 | H | H | CH$_3$ | C$_2$H$_5$ |
| 4.7 | CH$_3$ | CH$_3$ | CF$_3$ | CH$_3$ |
| 4.8 | CH$_3$ | CH$_3$ | CF$_2$H | CH$_3$ |

TABLE 5

Compounds of formula (IE)

(IE) cis/trans mixture

| Compound Number | R$^1$ | R$^2$ | R$^3$ |
|---|---|---|---|
| 5.1 | H | H | CF$_3$ |
| 5.2 | H | H | Cl |
| 5.3 | H | H | Br |
| 5.4 | CH$_3$ | CH$_3$ | CF$_3$ |
| 5.5 | CH$_3$ | CH$_3$ | Cl |
| 5.6 | CH$_3$ | CH$_3$ | Br |

TABLE 6

Compounds of formula (IF)

(IF) cis/trans mixture

| Compound Number | R$^1$ | R$^2$ | R$^3$ |
|---|---|---|---|
| 6.1 | H | H | CF$_3$ |
| 6.2 | H | H | CH$_3$ |
| 6.3 | CH$_3$ | CH$_3$ | CF$_3$ |
| 6.4 | CH$_3$ | CH$_3$ | CH$_3$ |

TABLE 7

Compounds of formula (IG)

(IG) cis compound

| Compound Number | R$^1$ | R$^2$ | R$^3$ | R$^4$ | R$^5$ |
|---|---|---|---|---|---|
| 7.1 | H | H | CF$_3$ | CH$_3$ | H |
| 7.2 | H | H | CF$_2$H | CH$_3$ | H |
| 7.3 | H | H | CFH$_2$ | CH$_3$ | H |
| 7.4 | H | H | CH$_3$ | CH$_3$ | F |
| 7.5 | H | H | CH$_3$ | CH$_3$ | Cl |
| 7.6 | H | H | CF$_3$ | C$_2$H$_5$ | H |
| 7.7 | H | H | CF$_2$H | C$_2$H$_5$ | H |
| 7.8 | H | H | CFH$_2$ | C$_2$H$_5$ | H |
| 7.9 | H | H | CH$_3$ | C$_2$H$_5$ | F |
| 7.10 | H | H | CH$_3$ | C$_2$H$_5$ | Cl |
| 7.11 | CH$_3$ | CH$_3$ | CF$_3$ | CH$_3$ | H |
| 7.12 | CH$_3$ | CH$_3$ | CF$_2$H | CH$_3$ | H |

TABLE 8

Compounds of formula (IH)

(IH) cis compound

| Compound Number | R$^1$ | R$^2$ | R$^3$ | R$^4$ | R$^5$ |
|---|---|---|---|---|---|
| 8.1 | H | H | CF$_3$ | CH$_3$ | H |
| 8.2 | H | H | CF$_2$H | CH$_3$ | H |
| 8.3 | H | H | CFH$_2$ | CH$_3$ | H |
| 8.4 | H | H | CH$_3$ | CH$_3$ | F |
| 8.5 | H | H | CH$_3$ | CH$_3$ | Cl |
| 8.6 | H | H | CF$_3$ | C$_2$H$_5$ | H |
| 8.7 | H | H | CF$_2$H | C$_2$H$_5$ | H |
| 8.8 | H | H | CFH$_2$ | C$_2$H$_5$ | H |
| 8.9 | H | H | CH$_3$ | C$_2$H$_5$ | F |
| 8.10 | H | H | CH$_3$ | C$_2$H$_5$ | Cl |
| 8.11 | CH$_3$ | CH$_3$ | CF$_3$ | CH$_3$ | H |
| 8.12 | CH$_3$ | CH$_3$ | CF$_2$H | CH$_3$ | H |

TABLE 9

Compounds of Formula (Ii)

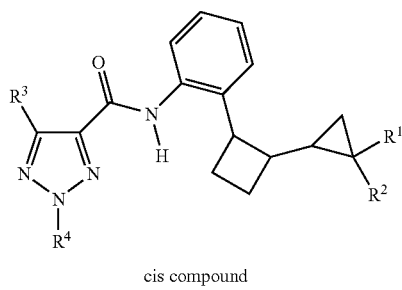

cis compound

| Compound Number | R¹ | R² | R³ | R⁴ |
|---|---|---|---|---|
| 9.1 | H | H | $CF_3$ | $CH_3$ |
| 9.2 | H | H | $CF_2H$ | $CH_3$ |
| 9.3 | H | H | $CFH_2$ | $CH_3$ |
| 9.4 | H | H | $CH_3$ | $CH_3$ |
| 9.5 | H | H | $CF_3$ | $C_2H_5$ |
| 9.6 | H | H | $CF_2H$ | $C_2H_5$ |
| 9.7 | H | H | $CFH_2$ | $C_2H_5$ |
| 9.8 | H | H | $CH_3$ | $C_2H_5$ |
| 9.9 | $CH_3$ | $CH_3$ | $CF_3$ | $CH_3$ |
| 9.10 | $CH_3$ | $CH_3$ | $CF_2H$ | $CH_3$ |

TABLE 10

Compounds of formula (IJ)

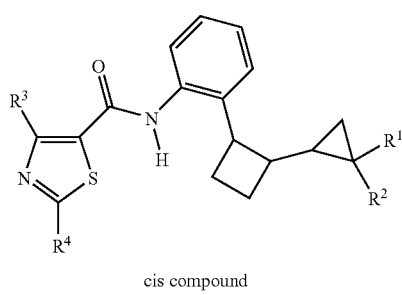

cis compound

| Compound Number | R¹ | R² | R³ | R⁴ |
|---|---|---|---|---|
| 10.1 | H | H | $CF_3$ | $CH_3$ |
| 10.2 | H | H | $CF_2H$ | $CH_3$ |
| 10.3 | H | H | $CH_3$ | $CH_3$ |
| 10.4 | H | H | $CF_3$ | $C_2H_5$ |
| 10.5 | H | H | $CF_2H$ | $C_2H_5$ |
| 10.6 | H | H | $CH_3$ | $C_2H_5$ |
| 10.7 | $CH_3$ | $CH_3$ | $CF_3$ | $CH_3$ |
| 10.8 | $CH_3$ | $CH_3$ | $CF_2H$ | $CH_3$ |

TABLE 11

Compounds of formula (IK)

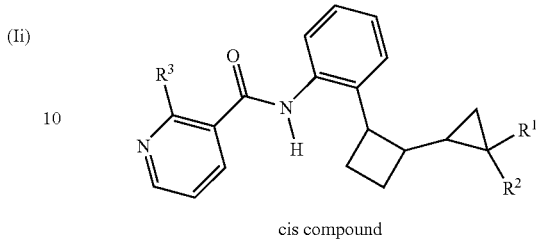

cis compound

| Compound Number | R¹ | R² | R³ |
|---|---|---|---|
| 11.1 | H | H | $CF_3$ |
| 11.2 | H | H | Cl |
| 12.3 | H | H | Br |
| 12.4 | $CH_3$ | $CH_3$ | $CF_3$ |
| 12.5 | $CH_3$ | $CH_3$ | Cl |
| 12.6 | $CH_3$ | $CH_3$ | Br |

TABLE 12

Compounds of formula (IL)

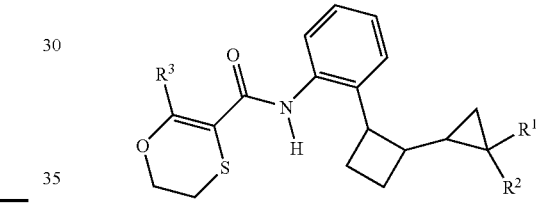

cis compound

| Compound Number | R¹ | R² | R³ |
|---|---|---|---|
| 12.1 | H | H | $CF_3$ |
| 12.2 | H | H | $CH_3$ |
| 12.3 | $CH_3$ | $CH_3$ | $CF_3$ |
| 12.4 | $CH_3$ | $CH_3$ | $CH_3$ |

Table 13: Characterising Data

Table 13 shows selected melting point and selected NMR data for compounds of Tables 1 to 12. $CDCl_3$ was used as the solvent for NMR measurements, unless otherwise stated. If a mixture of solvents was present, this is indicated as, for example: $CDCl_3/d_6$-DMSO). No attempt is made to list all characterising data in all cases.

In Table 13 and throughout the description that follows, temperatures are given in degrees Celsius; "NMR" means nuclear magnetic resonance spectrum; MS stands for mass spectrum; "%" is percent by weight, unless corresponding concentrations are indicated in other units. The following abbreviations are used throughout this description:

| | |
|---|---|
| m.p. = melting point | b.p. = boiling point. |
| S = singlet | br = broad |
| d = doublet | dd = doublet of doublets |
| t = triplet | q = quartet |
| m = multiplet | ppm = parts per million |

TABLE 13

| Compound Number | $^1$H-NMR data: (ppm/multiplicity/number of Hs) | m.p. (° C.) |
|---|---|---|
| 1.1 | | 160-162 |
| 1.2 | | 137-139 |
| 2.1 | | 167-169 |
| 4.1 | | 135-138 |
| 5.2 | | 148-150 |
| 7.2 | | 88-91 |
| 8.1 | | 100-104 |
| 10.1 | | 90-92 |

Compounds of the general formula (I):

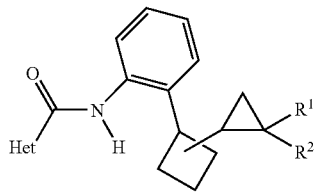
(I)

where Het, $R^1$ and $R^2$ have the meanings given above, may be prepared by reacting a compound of the formula Het-C(O)R, where R is halogen, hydroxy or $C_{1-6}$ alkoxy, but preferably chloro, with a compound of the formula (II) or the formula (III), depending on whether the cyclopropyl ring is attached to the 2- or 3-position of the cyclobutyl ring:

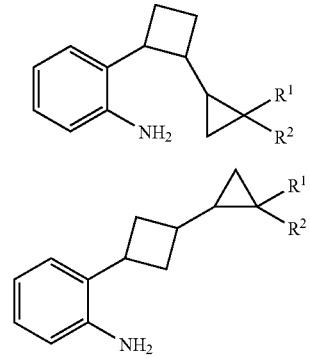

The reaction is carried out in the presence of a base, such as triethylamine, Hünigs base, sodium bicarbonate, sodium carbonate, potassium carbonate, pyridine or quinoline, but preferably triethylamine, and in a solvent, such as diethylether, tert-butyl methyl ether, tetrahydrofuran, methylene chloride, chloroform, N,N-dimethylformamide or N-methylpyrrolidinone, for between 10 minutes and 48 hours, preferably 12 to 24 hours, and between 0° C. and reflux, preferably 20 to 25° C. When R is hydroxy, a coupling agent such as benzotriazol-1-yloxytris(dimethylamino)phosphoniumhexafluorophosphate, bis-(2-oxo-3-oxazolidinyl)-phosphinic acid chloride, N,N'-dicyclohexylcarbodiimide or 1,1'-carbonyl-diimidazole, or an activating agent, such as oxalylic acid chloride, may be used.

The o-substituted anilines (II) and (III) may be prepared as described below with reference to Schemes 1 and 2.

Scheme 1

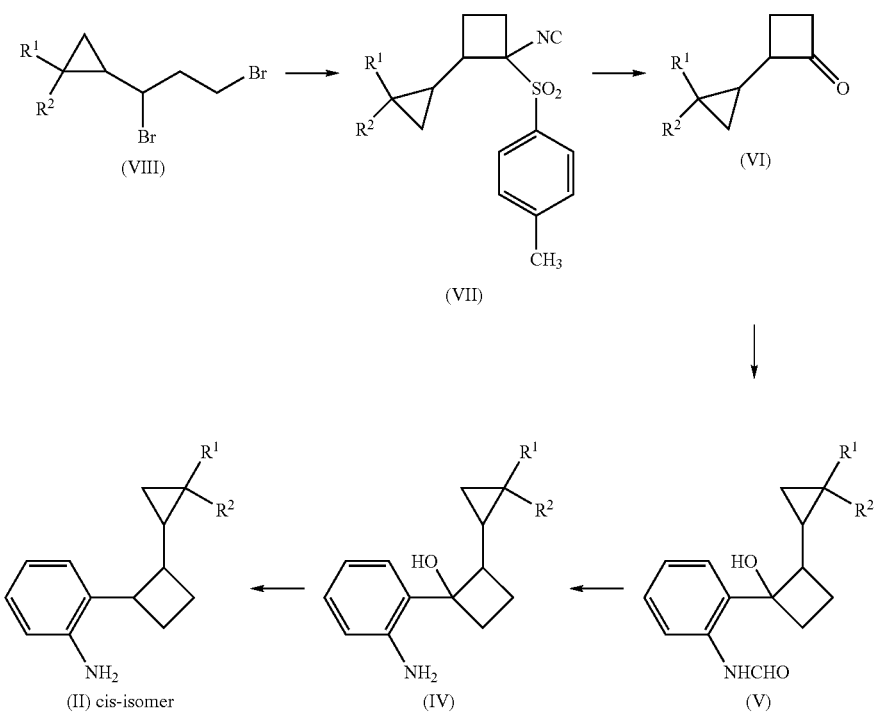

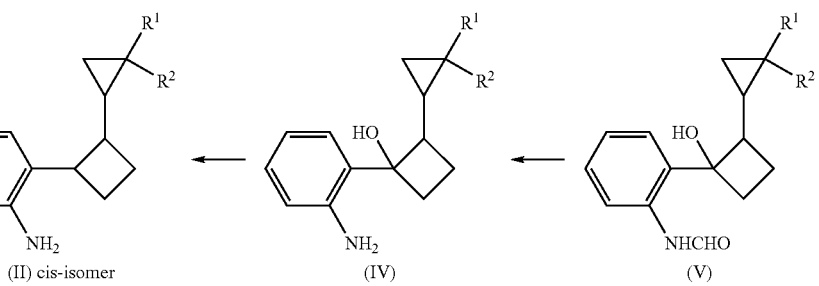

As shown in Scheme 1, a compound of the general formula (II), where R¹ and R² are as defined above, may be synthesized by dehydroxylating a cyclobutanol of formula (IV), for example, by hydrogenation in the presence of a strong acid, such as sulphuric acid, and a catalyst, such as palladium on carbon. The cyclobutanol (IV) may be prepared by treating a formamide (V) with a strong base, such as potassium hydroxide, in a suitable solvent, such as methanol, typically at the reflux temperature of the solvent. The formamide (V) may be prepared from a 2-cyclopropylcyclobutan-1-one (VI) by reaction at low temperature, typically at about −100° C., with N-(2-bromophenyl)formamide which, dissolved in a suitable solvent, such as a mixture of tetrahydrofuran and diethyl ether, is first mixed at low temperature with solutions of methyl- and n-butyllithium. The synthesis of the 2-cyclopropylcyclobutan-1-one (VI), where R¹ and R² are both H, is described in the Ph.D. thesis of G. Auchter (University of Tübingen, 1983). 2-Cyclopropylcyclobutan-1-ones, where R¹ and R² have other values as defined above, may be prepared in similar fashion from the corresponding (1,3-dibromopropyl)cyclopropane (VIII). Accordingly, the 2-cyclopropylcyclobutan-1-one (VI) may be prepared by treating a 1-(2-cyclopropyl-1-isocyanocyclobutanesulfonyl)-4-methyl benzene (VII) in a suitable solvent, such as sulfolane, with sulphuric acid at room temperature. The compound (VII) may be prepared from a (1,3-dibromopropyl)cyclopropane (VIII) by reaction with 1-isocyanomethanesulfonyl-4-methylbenzene (TosMIC) in the presence of a strong base, such as sodium hydride or potassium tert-butoxide in a suitable solvent or solvent mixture, such as tetrahydrofuran or diethyl ether with dimethyl sulfoxide.

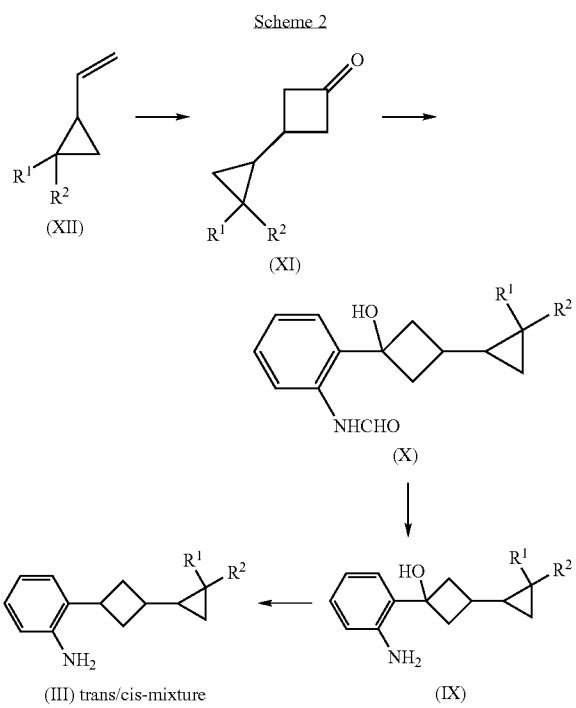

Scheme 2

(XII) → (XI) → (X) → (IX) → (III) trans/cis-mixture

As shown in Scheme 2, a compound of the general formula (III), where R¹ and R² are as defined above, may be synthesized from a 3-cyclopropylcyclobutan-1-one (XI) via a formamide (X) and butanol (IX) in a similar manner to that described above for the synthesis of the compound (II) from the 2-cyclopropylcyclobutan-1-one (VI) via the formamide (V) and butanol (IV). The synthesis of the 2-cyclopropylcyclobutanone (VI), where R¹ and R² are both H, is described in the Ph.D. thesis of G. Auchter (University of Tübingen, 1983). 3-Cyclopropylcyclobutan-1-ones, where R¹ and R² have other values as defined above, may be prepared in similar fashion from the corresponding vinylcyclo-propane (XII). Accordingly, the 3-cyclopropylcyclobutan-1-one (XI) may be prepared in two steps. First, the vinylcyclopropane (XII) is reacted at an elevated temperature with dichloroacetylchloride in a suitable solvent, such as n-pentane, in the presence of a suitable base, such as triethylamine. The crude 2,2-dichloro-3-cyclopropylcyclobutan-1-one so obtained, may without purification, be treated with a zinc/acetic acid mixture at an elevated temperature to form the desired 3-cyclopropylcyclobutan-1-one (XI).

The starting materials (VIII) and (XII) are either available from commercial sources or may be prepared by methods well documented in the literature.

The o-substituted anilnes (II) and (III) are novel compounds and are include in the present invention. Thus according to still yet another aspect of the present invention there is provided a compound of the general formula (II) or of the general formula (III):

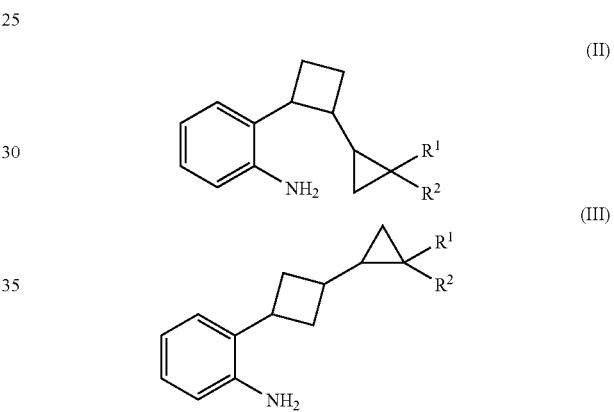

where R¹ and R² are independently H, halo, $C_{1-4}$ alkyl or $C_{1-4}$ haloalkyl.

Normally R¹ and R² will be the same. Typically, they are both H or both $C_{1-4}$ alkyl, and usually both H or both methyl. The invention includes the cis and trans isomers of both compounds (II) and (III), either as single isomers or as mixtures of isomers in any proportion. In particular, the invention includes the cis isomers of compounds of the formula (II) and trans/cis mixtures of compounds of the formula (III), and especially the cis isomers of compounds of the formula (II) where R¹ and R² are both H or both methyl and trans/cis mixtures of compounds of the formula (III) where R¹ and R² are both H or both methyl.

It has now been found that the compounds of formula (I) according to the invention have, for practical purposes, a very advantageous spectrum of activities for protecting useful plants against diseases that are caused by phytopathogenic microorganisms, such as fungi, bacteria or viruses.

The invention relates to a method of controlling or preventing infestation of useful plants by phytopathogenic microorganisms, wherein a compound of formula (I) is applied as active ingredient to the plants, to parts thereof or the locus thereof. The compounds of formula (I) according to the invention are distinguished by excellent activity at low rates of application, by being well tolerated by plants and by being environmentally safe. They have very useful curative, preventive and systemic properties and are used for protecting numerous useful plants. The compounds of formula (I) can be used to inhibit or destroy the diseases that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula (I) as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compounds of formula (I) according to the invention may be used for controlling fungi in related areas, for example in the protection of technical materials, including wood and wood related technical products, in food storage or in hygiene management.

The compounds of formula (I) are, for example, effective against the phytopathogenic fungi of the following classes: Fungi imperfecti (e.g. *Botrytis, Pyricularia, Helminthosporium, Fusarium, Septoria, Cercospora* and *Alternaria*) and Basidiomycetes (e.g. *Rhizoctonia, Hemileia, Puccinia*). Additionally, they are also effective against the Ascomycetes classes (e.g. *Venturia* and *Erysiphe, Podosphaera, Monilinia, Uncinula*) and of the Oomycetes classes (e.g. *Phytophthora, Pythium, Plasmopara*). Good activity has been observed against rust diseases, such as *Puccinia recondita* spp. Furthermore, the novel compounds of formula (I) are effective against phytopathogenic bacteria and viruses (e.g. against *Xanthomonas* spp, *Pseudomonas* spp, *Erwinia amylovora* as well as against the tobacco mosaic virus).

Within the scope of the invention, useful plants to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, *cinnamomum*, camphor) or plants such as tobacco, nuts, coffee, eggplants, sugar cane, tea, pepper, vines, hops, bananas and natural rubber plants, as well as ornamentals.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfinuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compounds of formula (I) can be used in unmodified form or, preferably, together with carriers and adjuvants conventionally employed in the art of formulation.

Therefore the invention also relates to compositions for controlling and protecting against phytopathogenic microorganisms, comprising a compound of formula (I) and an inert carrier, and to a method of controlling or preventing infestation of useful plants by phytopathogenic microorganisms, wherein a composition, comprising a compound of formula (I) as active ingredient and an inert carrier, is applied to the plants, to parts thereof or the locus thereof.

To this end compounds of formula (I) and inert carriers are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula (I) or compositions, comprising a compound of formula (I) as active ingredient and an inert carrier, can be applied to the locus of the plant or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

A preferred method of applying a compound of formula (I), or a composition, comprising a compound of formula (I) as active ingredient and an inert carrier, is foliar application. The frequency of application and the rate of application will depend on the risk of infestation by the corresponding pathogen. However, the compounds of formula (I) can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula (I) may also be applied to seeds (coating) by impregnating the seeds or tubers either with a liquid formulation of the fungicide or coating them with a solid formulation.

A formulation, i.e. a composition comprising the compound of formula (I) and, if desired, a solid or liquid adjuvant, is prepared in a known manner, typically by intimately mixing and/or grinding the compound with extenders, for example solvents, solid carriers and, optionally, surface-active compounds (surfactants).

The agrochemical formulations will usually contain from 0.1 to 99% by weight, preferably from 0.1 to 95% by weight, of the compound of formula (I), 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient rates of application are from 10 mg to 1 g of active substance per kg of seeds. The rate of application for the desired action can be determined by experiments. It depends for example on the type of action, the developmental stage of the useful plant, and on the application (location, timing, application method) and can, owing to these parameters, vary within wide limits.

The compounds of formula (I), or a pharmaceutical salt thereof, described above may also an advantageous spectrum of activity for the treatment and/or prevention of microbial infection in an animal.

"Animal" can be any animal, for example, insect, mammal, reptile, fish, amphibian, preferably mammal, most preferably human. "Treatment" means the use on an animal which has microbial infection in order to reduce or slow or stop the increase or spread of the infection, or to reduce the infection or to cure the infection. "Prevention" means the use on an animal which has no apparent signs of microbial infection in order to prevent any future infection, or to reduce or slow the increase or spread of any future infection.

According to the present invention there is provided the use of a compound of formula (I) in the manufacture of a medicament for use in the treatment and/or prevention of microbial infection in an animal. There is also provided the use of a compound of formula (I) as a pharmaceutical agent. There is also provided the use of a compound of formula (I) as an antimicrobial agent in the treatment of an animal. According to the present invention there is also provided a pharmaceutical composition comprising as an active ingredient a compound of formula (I), or a pharmaceutically acceptable salt thereof, and a pharmaceutically acceptable diluent or carrier. This composition can be used for the treatment and/or prevention of antimicrobial infection in an animal. This pharmaceutical composition can be in a form suitable for oral administration, such as tablet, lozenges, hard capsules, aqueous suspensions, oily suspensions, emulsions dispersible powders, dispersible granules, syrups and elixirs. Alternatively this pharmaceutical composition can be in a form suitable for topical application, such as a spray, a cream or lotion. Alternatively this pharmaceutical composition can be in a form suitable for parenteral administration, for example injection. Alternatively this pharmaceutical composition can be in inhalable form, such as an aerosol spray.

The compounds of formula (I) may be effective against various microbial species able to cause a microbial infection in an animal. Examples of such microbial species are those causing Aspergillosis such as *Aspergillus fumigatus, A. flavus, A. terrus, A. nidulans* and *A. niger*; those causing Blastomycosis such as *Blastomyces dermatitidis*; those causing Candidiasis such as *Candida albicans, C. glabrata, C. tropicalis, C. parapsilosis, C. krusei* and *C. lusitaniae*; those causing Coccidioidomycosis such as *Coccidioides immitis*; those causing Cryptococcosis such as *Cryptococcus neoformans*; those causing Histoplasmosis such as *Histoplasma capsulatum* and those causing Zygomycosis such as *Absidia corymbifera, Rhizomucor pusillus* and *Rhizopus arrhizus*. Further examples are *Fusarium* Spp such as *Fusarium oxysporum* and *Fusarium solani* and *Scedosporium* Spp such as *Scedosporium apiospermum* and *Scedosporium prolificans*. Still further examples are *Microsporum* Spp, *Trichophyton* Spp, *Epidermophyton* Spp, *Mucor* Spp, *Sporothorix* Spp, *Phialophora* Spp, *Cladosporium* Spp, *Petriellidium* spp, *Paracoccidioides* Spp and *Histoplasma* Spp.

The following non-limiting Examples illustrate the above-described invention in more detail. Abbreviations used in the Examples, not previously explained, are detailed below.

TosMIC=1-isocyanomethanesulfonyl-4-methylbenzene

DMSO=dimethyl sulfoxide

DMF=dimethylformamide

EXAMPLE 1

This Example Illustrates the Preparation of 1-(2-cyclopropyl-1-isocyanocyclobutane-sulfonyl)-4-methylbenzene (an Intermediate Compound of the Formula (VII))

In a sulfonation flask 11.1 g (0.28 mol) sodium hydride was suspended in a mixture of 80 ml diethylether and 220 ml DMSO. Then a solution of 19.9 g (0.1 mol) TosMIC and 28.2 g (0.115 mol) (1.3-dibromopropyl)cyclopropane in 30 ml diethylether and 80 ml DMSO was added in 90 minutes. After stirring for 1.5 hours, 70 ml of water was added slowly under ice cooling. The first crop of product was filtered off (16.3 g) and the mother liquor evaporated. The raw material obtained from the mother liquor was then purified by flash chromatography over silicagel (eluent: hexane/ethylacetate 2:1). Overall yield: 19.0 g (68% of theory) of 1-(2-cyclopropyl-1-isocyanocyclobutanesulfonyl)-4-methylbenzene in the form of a solid.

EXAMPLE 2

This Example Illustrates the Ireparation of 2-cyclopropylcyclobutan-1-one (an Intermediate Compound of the Formula (VI))

In a sulfonation flask 19.0 g (0.069 mol) 1-(2-cyclopropyl-1-isocyanocyclobutane-sulfonyl)-4-methylbenzene (from Example 1) were suspended in 75 ml of sulfolane. Then a mixture containing 4 ml of water and 4 ml of concentrated sulphuric acid was added slowly (10 minutes) under ice cooling in such a manner that the internal temperature remained constant between 20-25° C. After stirring for 10 minutes 140 ml of a concentrated sodium bicarbonate solution was added and the resulting mixture extracted 2 times continuously with n-pentane in a Kutscher-Steudel apparatus. After distilling off the solvent and condensation of the product at 0.2 mbar in a cold trap, the pure product was obtained. Yield: 3.6 g (47% of theory) of 2-cylopropyl-butan-1-one in the form of a colourless liquid.

EXAMPLE 3

This Example Illustrates the Preparation of N-[2-(2-cyclopropyl-1-hydroxycyclobutyl)-phenyl]Formamide (an Intermediate Compound of the Formula (V))

In a sulfonation flask, 7.8 g (0.039 mol) N-(2-bromophenyl)formamide was dissolved in a mixture of 150 ml dry tetrahydrofuran and 150 ml dry diethyl ether. The solution was cooled to −70° C. and 25.6 ml (0.041 mol) methyllithium solution (1.6M in diethyl ether) added in 30 minutes in such a manner that the internal temperature remained constant at −70° C. Then the resulting solution was cooled to −100° C. and 25.6 ml (0.041 mol) of n-butyllithium solution (1.6M in hexane) was added in such a manner that the internal temperature remained constant at −100° C. (±2° C.). After stirring for 2 hours at −70 to −75° C., the solution was again cooled to −100° C. and 4.54 g (0.041 mol) 2-cyclopropylcyclobutan-1-one (prepared as described in Example 2) dissolved in 30 ml of dry tetrahydrofuran, was added slowly (20 minutes) at an internal temperature of −100° C. After stirring for 3 hours at −75° C., the temperature was elevated to 0° C. in ca. 30 minutes. After the addition of concentrated ammonium chloride solution, ethyl acetate was added and the organic phase was washed several times with water. After drying and evaporation of the solvent in a water jet vacuum, the crude material was obtained. Purification was achieved by flash chromatography over silica gel (eluant: hexane/ethyl acetate 1:1). Yield: 3.4 g (38% of theory) of N-[2-(2-cyclopropyl-1-hydroxycyclo-butyl)-phenyl]formamide in the form of a slightly yellow liquid.

EXAMPLE 4

This Example Illustrates the Preparation of 1-(2-aminophenyl)-2-cyclopropylcyclobutanol (An Intermediate Compound of the Formula (IV))

In a sulfonation flask, a mixture consisting of 3.35 g (0.0145 mol) N-[2-(2-cyclopropyl-1-hydroxycyclobutyl) phenyl]-formamide (prepared as described in Example 3), 1.3 g (0.02 mol) potassium hydroxide and 25 ml methanol was stirred at reflux temperature for 3 hours. Then the solvent was distilled off in a water jet vacuum and the residue taken up in 100 ml of ethyl acetate. The organic phase was washed three times with water and after drying with sodium sulphate the solvent was distilled off in a water jet vacuum. The raw material was purified by flash chromatography over silica gel (eluant: hexane/ethyl acetate 2:1). Yield: 2.4 g (80% of theory) of 1-(2-aminophenyl)-2-cyclopropylcyclobutanol in the form of a slightly brownish oil ($^1$HNMR (CDCl$_3$): 0.2-0.36 ppm/m/2H, 0.55 ppm/m/2H), 1.08 ppm/m/1H), 1.81 ppm/m/2H, 2.3-2.48 ppm/m/3H, 4.2 ppm (broad)/3H–NH$_2$+OH), 6.6-6.72 ppm/m/2H, 7.05-7.15/m/2H– only one isomer obtained).).

EXAMPLE 5

This Example Illustrates the Preparation of 2-(2-cyclopropylcyclobutyl)phenylamine (An Intermediate Compound of the Formula (II))

2.3 g (0.0113 mol) 1-(2-Aminophenyl)-2-cyclopropylcyclobutanol (prepared as described in Example 4) was dissolved in 40 ml of ethanol, 3.25 g sulphuric acid (96%) was added and after the addition of 500 mg of 10% Pd on charcoal, the mixture was hydrogenated for 1 hour at room temperature. After removal of the catalyst, ethanol was distilled off in a water jet vacuum and the residue purified by flash chromatography over silica gel (eluant: hexane/ethyl acetate 4:1). Yield: 1.88 g (89% of theory) of the cis isomer of 2-(2-cyclopropylcyclobutyl)phenylamine in form of a yellow oil ($^1$HNMR (CDCl$_3$): −0.1-0.05 ppm/m/2H, 0.19 ppm/m/1H, 0.27 ppm/m/1H, 0.55 ppm/m/1H, 1.65 ppm/m/1H, 2.15 ppm/m/3H, 2.52 ppm/m/1H, 3.55 ppm (broad)/2H –NH$_2$, 6.68 ppm/d/1H, 6.80 ppm/t/1H, 7.08 ppm/t/1H, 7.18 ppm/d/1H).

EXAMPLE 6

This Example Illustrates the Preparation of 1-methyl-4-trifluoromethyl-1H-pyrrole-3-carboxylic acid[2-(2-cyclopropylcyclobutyl)phenyl]amide (Compound No. 2.1)

190 mg (1 mmol) 1-Methyl-trifluoromethyl-1H-pyrrole-3-carboxylic acid and 140 mg (1.05 mmol) oxalylic acid chloride were dissolved in 10 ml methylene chloride. The solution was stirred for 3 hours at room temperature in the presence of catalytic amounts of DMF. Then the resulting reaction mixture was slowly added to a solution consisting of 190 mg (1 mmol) 2-(2-cyclopropylcyclobutyl)phenylamine (prepared as described in Example 5), 200 mg (2 mmol) of triethylamine and 10 ml methylene chloride. After stirring for 16 hours at room temperature the solvent was distilled off and the raw material purified by flash chromatography over silica gel (eluant: hexane/methylene chloride/ethyl acetate 2:2:1). Yield: 240 mg (66% of theory) of 1-methyl-4-trifluoromethyl-1H-pyrrole-3-carboxylic acid [2-(2-cyclopropylcyclobutyl)phenyl]amide (cis-isomer) in the form of slightly yellow crystals (mp.: 167-169° C.).

EXAMPLE 7

This Example Illustrates the Preparation of 3-cyclopropylcyclobutan-1-one (An Intermediate Compound of the Formula (XI)

In a sulfonation flask, 11.8 g (0.173 mol) vinylcyclopropane and 76.5 g (0.52 mol) dichloroacetylchloride were dissolved in 700 ml of n-pentane. Then 35.0 g (0.35 mol) triethylamine were added over a period of 1 hour. The mixture was heated at reflux temperature for 16 hours (cooling of the reflux condenser with a cryostate was necessary). The reaction mixture was diluted with ice water and the organic layer separated. The water phase was extracted three times with diethyl ether and then all the organic phases were combined. After washing with sodium bicarbonate solution and brine, the organic layer was dried over sodium sulphate. Distilling off the solvent in a water jet vacuum gave the raw material (52 g of 2.2-dichloro-3-cyclopropylcyclo-butane-1-one), which was used without purification in the next step.

In a sulfonation flask, 70 g (0.173 mol) zinc was added to 250 ml of acetic acid at room temperature. 52 g of the raw material obtained in the first step, was dissolved in 50 ml acetic acid and added to the zinc/acetic acid mixture over a period of 2 hours. Then the mixture was stirred at 65° C. for 5 hours. After filtration, the liquid phase was diluted with water and extracted several times with diethyl ether. Drying of the organic phase over sodium sulphate and evaporation of the solvent in a water jet vacuum, gave the crude material, which was purified by distillation. Yield: 4.1 g (21% of theory) of 3-cylopropylcyclobutan-1-one in the form of a colourless liquid (bp.: 53-57° C./20 mbar)

EXAMPLE 8

This Example Illustrates the Preparation of N-[2-(3-cyclopropyl-1-hydroxycyclobutyl)-phenyl]Formamide (An Intermediate Compound of the Formula (X))

In a sulfonation flask, 7.8 g (0.039 mol) N-(2-bromophenyl)form amide was dissolved in a mixture of 100 ml dry tetrahydrofuran. The solution was cooled to −100° C. and 60 ml (0.096 mol) of n-butyllithium solution (1.6M in hexane) was added over a period of 1 hour in such at manner that the internal temperature remained constant at −100° C. (±2° C.). After stirring for 2.5 hours at −100° to −110° C., 5.3 g (0.048 mmol) of 3-cyclopropylcyclobutan-1-one (prepared as described in Example 7), dissolved in 30 ml of dry tetrahydrofuran, were added over a period of 30 minutes in such a manner that the internal temperature remained constant at −100° C. (±2° C.). After stirring for 3 hours at −78° C., the temperature was elevated to 0° C. in ca. 30 minutes. Concentrated ammonium chloride solution and ethyl acetate were added and the organic phase was washed several times with water. After drying and evaporation of the solvent in a water jet vacuum, the crude material was obtained. Purification was achieved by flash chromatography over silica gel (eluant: hexane/ethyl acetate 1:1). Yield: 2.55 g (23% of theory) of N-[2-(3-cyclopropyl-1-hydroxycyclobutyl)-phenyl]formamide in the form of a resin.

EXAMPLE 9

This Example Illustrates the Preparation of 1-(2-aminophenyl)-3-cyclopropylcyclobutanol (An Intermediate Compound of the Formula (IX))

In a sulfonation flask, a mixture consisting of 2.5 g (0.0108 mol) N-[2-(3-cyclopropyl-1-hydroxy-cyclobutyl)phenyl]-formamide (prepared as described in Example 8), 1.4 g (0.021 mol) potassium hydroxide and 25 ml methanol was stirred at reflux temperature for 4 hours. Then the solvent was distilled off in a water jet vacuum and the residue taken up in 100 ml of ethyl acetate. The organic phase was washed three times with water and after drying with sodium sulphate the solvent was distilled off in a water jet vacuum. The crude material was purified by flash chromatography over silica gel (eluant: hexane/ethylacetate 1:1). Yield: 1.65 g (75% of theory) of 1-(2-aminophenyl)-3-cyclopropylcyclobutanol in the form of a slightly brownish solid (mp.: 58-61° C.).

EXAMPLE 10

This Example Illustrates the Preparation of 2-(3-cyclopropylcyclobutyl)phenylamine (An Intermediate Compound of the Formula (III))

1.22 g (0.006 mol) 1-(2-aminophenyl)-3-cyclopropylcyclobutanol (prepared as described in Example 9) was dissolved in 40 ml of ethanol, 1.72 g sulphuric acid (96%) were added and after addition of 250 mg of 10% Pd on charcoal, the mixture was hydrogenated for 5.5 hours at room temperature. After removal of the catalyst, ethanol was distilled off in a water jet vacuum and the residue purified by flash chromatography over silica gel (eluent: hexane/ethyl acetate 5:1). Yield: 0.94 g (82% of theory) of a cis/trans mixture of 2-(3-cyclopropylcyclobutyl)phenylamine in the form of a yellow oil (MS: $M^+$-peak of 187).

Formulation Examples for Compounds of Formula (I)

Example F-1.1 to F-1.3

Emulsifiable Concentrates

| Components | F-1.1 | F-1.2 | F-1.3 |
|---|---|---|---|
| compound of Tables 1 to 12 | 25% | 40% | 50% |
| calcium dodecylbenzenesulfonate | 5% | 8% | 6% |
| castor oil polyethylene glycol ether (36 mol ethylenoxy units) | 5% | — | — |
| tributylphenolpolyethylene glycol ether (30 mol ethylenoxy units) | — | 12% | 4% |
| cyclohexanone | — | 15% | 20% |
| xylene mixture | 65% | 25% | 20% |

Emulsions of any desired concentration can be prepared by diluting such concentrates with water.

Example F-2

Emulsifiable Concentrate

| Components | F-2 |
|---|---|
| compound of Tables 1 to 12 | 10% |
| octylphenolpolyethylene glycol ether (4 to 5 mol ethylenoxy units) | 3% |
| calcium dodecylbenzenesulfonate | 3% |
| castor oil polyglycol ether (36 mol ethylenoxy units) | 4% |
| cyclohexanone | 30% |
| xylene mixture | 50% |

Emulsions of any desired concentration can be prepared by diluting such concentrates with water.

Examples F-3.1 to F-3.4

Solutions

| Components | F-3.1 | F-3.2 | F-3.3 | F-3.4 |
|---|---|---|---|---|
| compound of Tables 1 to 12 | 80% | 10% | 5% | 95% |
| propylene glycol monomethyl ether | 20% | — | — | — |
| polyethylene glycol (relative molecular mass: 400 atomic mass units) | — | 70% | — | — |
| N-methylpyrrolid-2-one | — | 20% | — | — |
| epoxidised coconut oil | — | — | 1% | 5% |
| benzin (boiling range: 160-190°) | — | — | 94% | — |

The solutions are suitable for use in the form of microdrops.

Examples F-4.1 to F-4.4

Granulates

| Components | F-4.1 | F-4.2 | F-4.3 | F-4.4 |
|---|---|---|---|---|
| compound of Tables 1 to 12 | 5% | 10% | 8% | 21% |
| kaolin | 94% | — | 79% | 54% |
| highly dispersed silicic acid | 1% | — | 13% | 7% |
| attapulgite | — | 90% | — | 18% |

The novel compound is dissolved in dichloromethane, the solution is sprayed onto the carrier and the solvent is then removed by distillation under vacuum.

Examples F-5.1 and F-5.2

Dusts

| Components | F-5.1 | F-5.2 |
|---|---|---|
| compound of Tables 1 to 12 | 2% | 5% |
| highly dispersed silicic acid | 1% | 5% |
| talcum | 97% | — |
| kaolin | — | 90% |

Ready for use dusts are obtained by intimately mixing all components.

Examples F-6.1 to F-6.3

Wettable Powders

| Components | F-6.1 | F-6.2 | F-6.3 |
|---|---|---|---|
| compound of Tables 1 to 12 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7 to 8 mol ethylenoxy units) | — | 2% | — |
| highly dispersed silicic acid | 5% | 10% | 10% |
| kaolin | 62% | 27% | — |

All components are mixed and the mixture is thoroughly ground in a suitable mill to give wettable powders which can be diluted with water to suspensions of any desired concentration.

Example F7

Flowable Concentrate for Seed Treatment

| | |
|---|---|
| compound of Tables 1 to 12 | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

BIOLOGICAL EXAMPLES

Fungicidal Actions

Example B-1

Action Against *Puccinia recondita*/Wheat (Brownrust on Wheat)

1 week old wheat plants cv. Arina are treated with the formulated test compound (0.02% active ingredient) in a spray chamber. One day after application, the wheat plants are inoculated by spraying a spore suspension ($1 \times 10^5$ uredospores/ml) on the test plants. After an incubation period of 2 days at 20° C. and 95% r.h. the plants are kept in a greenhouse for 8 days at 20° C. and 60% r.h. The disease incidence is assessed 10 days after inoculation.

Compounds 1.1, 1.2, 2.1, 4.1, 5.2, 7.2, 8.1 and 10.1 each show good activity in this test (<20% infestation).

Example B-2

Action Against *Podosphaera leucotricha*/Apple (Powdery Mildew on Apple)

5 week old apple seedlings cv. McIntosh are treated with the formulated test compound (0.02% active ingredient) in a spray chamber. One day after, the application apple plants are inoculated by shaking plants infected with apple powdery mildew above the test plants. After an incubation period of 12 days at 22° C. and 60% r.h. under a light regime of 14/10 hours (light/dark) the disease incidence is assessed.

Compounds 1.1, 1.2, 2.1, 4.1, 5.2, 7.2, 8.1 and 10.1 each exhibit strong efficacy (<20% infestation).

Example B-3

Action Against *Venturia inaequalis*/Apple (Scab on Apple)

4 week old apple seedlings cv. McIntosh are treated with the formulated test compound (0.02% active ingredient) in a spray chamber. One day after application, the apple plants are inoculated by spraying a spore suspension ($4 \times 10^5$ conidia/ml) on the test plants. After an incubation period of 4 days at 21° C. and 95% r.h. the plants are placed for 4 days at 21° C. and 60% r.h. in a greenhouse. After another 4 day incubation period at 21° C. and 95% r.h. the disease incidence is assessed.

Compounds 1.1, 1.2, 2.1, 4.1, 5.2, 7.2, 8.1 and 10.1 each exhibit strong efficacy (<20% infestation).

Example B-4

Action Against *Erysiphe graminis*/Barley (Powdery Mildew on Barley)

1 week old barley plants cv. Regina are treated with the formulated test compound (0.02% active ingredient) in a spray chamber. One day after application, the barley plants are inoculated by shaking powdery mildew infected plants above the test plants. After an incubation period of 6 days at 20° C./18° C. (day/night) and 60% r.h. in a greenhouse the disease incidence is assessed.

Compounds 1.1, 1.2, 2.1, 4.1, 5.2, 7.2, 8.1 and 10.1 each exhibit strong efficacy (<20% infestation).

Example B-5

Action Against *Botrytis cinerea*/Grape (*Botrytis* on Grapes)

5 week old grape seedlings cv. Gutedel are treated with the formulated test compound (0.02% active ingredient) in a spray chamber. Two days after application, the grape plants are inoculated by spraying a spore suspension ($1 \times 10^6$ conidia/ml) on the test plants. After an incubation period of 4 days at 21° C. and 95% r.h. in a greenhouse the disease incidence is assessed.

Compounds 1.1, 1.2, 2.1, 4.1, 5.2, 7.2, 8.1 and 10.1 each show good activity in this test (<50% disease incidence).

Example B-6

Action Against *Botrytis cinerea*/Tomato (*Botrytis* on Tomatoes)

4 week old tomato plants cv. Roter Gnom are treated with the formulated test compound (0.02% active ingredient) in a spray chamber. Two days after application, the tomato plants are inoculated by spraying a spore suspension ($1 \times 10^5$ conidia/ml) on the test plants. After an incubation period of 4 days at 20° C. and 95% r.h. in a growth chamber the disease incidence is assessed.

Compounds 1.1, 1.2, 2.1, 4.1, 5.2, 7.2, 8.1 and 10.1 each exhibit good efficacy (<50% disease incidence).

Example B-7

Action Against *Helminthosporium teres*/Barley (Net Blotch on Barley)

1 week old barley plants cv. Regina are treated with the formulated test compound (0.02% active ingredient) in a spray chamber. Two days after application, the barley plants are inoculated by spraying a spore suspension ($3 \times 10^4$ conidia/ml) on the test plants. After an incubation period of 4 days at 20° C. and 95% r.h. in a greenhouse the disease incidence is assessed.

Compounds 1.1, 1.2, 2.1, 4.1, 5.2, 7.2, 8.1 and 10.1 each show good activity in this test (<20% disease incidence).

Example B-8

Action Against *Alternaria solani*/Tomato (Early Blight on Tomatoes)

4 week old tomato plants cv. Roter Gnom are treated with the formulated test compound (0.02% active ingredient) in a spray chamber. Two days after application, the tomato plants are inoculated by spraying a spore suspension ($2 \times 10^5$ conidia/ml) on the test plants. After an incubation period of 3 days at 20° C. and 95% r.h. in a growth chamber the disease incidence is assessed.

Compounds 1.1, 1.2, 2.1, 4.1, 5.2, 7.2, 8.1 and 10.1 each show good activity in this test (<20% disease incidence).

Example B-9

Action Against *Uncinula necator*/Grape (Powdery Mildew on Grapes)

5 week old grape seedlings cv. Gutedel are treated with the formulated test compound (0.02% active ingredient) in a spray chamber. One day after application, the grape plants are inoculated by shaking plants infected with grape powdery mildew above the test plants. After an incubation period of 7 days at 26° C. and 60% r.h. under a light regime of 14/10 hours (light/dark) the disease incidence is assessed.

Compounds 1.1, 1.2, 2.1, 4.1, 5.2, 7.2, 8.1 and 10.1 each show good activity in this test (<20% disease incidence).

Example B-10

Action Against *Puccinia recondita*/Wheat (Brownrust on Wheat) (Pouch Test)

Formulated test compound (0.002% active ingredient) is applied into a pouch which is previously equipped with a filter paper. After the application wheat seeds (cv. Arina) are sown into the upper fault of the filter paper. The prepared pouches are then incubated at 23° C./18° C. (day/night) and 80% r.h. One week after sowing, the wheat plants are inoculated by spraying a spore suspension ($1 \times 10^5$ uredospores/ml) on the test plants. After an incubation period of 1 day at 23° C. and 95% r.h. the plants were kept for 9 days at 20° C./18° C. (day/night) and 80% r.h. The disease incidence is assessed 10 days after inoculation. The efficacy of each test compound is used as an indicator for systemic activity.

Compounds 1.1, 1.2, 2.1, 4.1, 5.2, 7.2, 8.1 and 10.1 each show good activity in this test (<50% disease incidence).

Example B-11

Action Against *Septoria tritici*/Wheat (*Septoria* Leaf Spot on Wheat)

2 week old wheat plants cv. Riband are treated with the formulated test compound (0.02% active ingredient) in a spray chamber. One day after application, wheat plants are inoculated by spraying a spore suspension ($10 \times 10^5$ conidia/ml) on the test plants. After an incubation period of 1 day at 23° C. and 95% r.h., the plants are kept for 16 days at 23° C. and 60% r.h. in a greenhouse. The disease incidence is assessed 18 days after inoculation.

Compounds 1.1, 1.2, 2.1, 4.1, 5.2, 7.2, 8.1 and 10.1 each show good activity in this test (<20% disease incidence).

The invention claimed is:
1. A compound of formula (I):

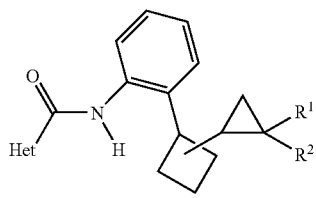

wherein:
Het is a 5- or 6-membered heterocyclic ring containing one to three heteroatoms, each independently selected from oxygen, nitrogen and sulphur, the ring being substituted by the groups $R^3$, $R^4$ and $R^5$;
$R^1$ and $R^2$ are each independently H, halo, $C_{1-4}$ alkyl or $C_{1-4}$ haloalkyl; and
$R^3$, $R^4$ and $R^5$ are each independently H, halo, $C_{1-4}$ alkyl, $C_{1-4}$ haloalkyl or $C_{1-4}$ haloalkoxy, provided that at least one of $R^3$, $R^4$ and $R^5$ is not H.

2. A compound of formula (I) according to claim 1, wherein $R^3$, $R^4$ and $R^5$ are each independently H, halo, $C_{1-4}$ alkyl or $C_{1-4}$ haloalkyl, provided that at least one of $R^3$, $R^4$ and $R^5$ is not H.

3. A compound of formula (I) according to claim 1, wherein $R^1$ and $R^2$ are both H or both $C_{1-4}$ alkyl.

4. A compound of formula (I) according to claim 1, wherein Het is pyrrolyl, pyrazolyl, thiazolyl, oxazolyl, imidazolyl, triazolyl, pyridyl, pyrimidinyl, pyridazinyl, 2,3-dihydro-[1,4]oxathiinyl, oxazinyl, thiazinyl or triazinyl.

5. A compound of formula (I) according to claim 1, wherein Het is pyrrol-3-yl substituted at the 1-position by $C_{1-4}$ alkyl, substituted at the 4-position by $C_{1-4}$ alkyl or $C_{1-4}$ haloalkyl and optionally substituted at the 2-position by halo; pyrazolyl-4-yl substituted at the 1-position by $C_{1-4}$ alkyl, substituted at 3-position by $C_{1-4}$ alkyl or $C_{1-4}$ haloalkyl and optionally substituted at the 5-position by halo; thiazol-5-yl or oxazol-5-yl substituted at the 2-position by $C_{1-4}$ alkyl and substituted at the 4-position by $C_{1-4}$ alkyl or $C_{1-4}$ haloalkyl; 2,3-dihydro[1,4]oxathiin-5-yl substituted at the 6-position by $C_{1-4}$ alkyl or $C_{1-4}$ haloalkyl; pyrid-3-yl substituted at the 2-position by halo or $C_{1-4}$ haloalkyl; or 2H-1,2,3-triazol-4-yl substituted at the 2-position by $C_{1-4}$ alkyl and at the 5-position by $C_{1-4}$ alkyl or $C_{1-4}$ haloalkyl; and $R^1$ and $R^2$ are both H or both $C_{1-4}$ alkyl.

6. A compound of formula (I) according to claim 1, wherein Het is 2-$C_{1-4}$ alkyl-4-$C_{1-4}$ haloalkylthiazol-5-yl, 2-halopyrid-3-yl, 1-$C_{1-4}$ alkyl-4-$C_{1-4}$ haloalkylpyrrol-3-yl or 1-$C_{1-4}$ alkyl-3-$C_{1-4}$ haloalkylpyrazol-4-yl; $R^1$ and $R^2$ are both hydrogen.

7. A compound of formula (I) according to claim 1, wherein Het is 2-methyl-4-trifluoromethylthiazol-5-yl, 2-chloropyrid-3-yl, 1-methyl-4-trifluoromethyl-pyrrol-3-yl, 1-methyl-3-trifluoromethylpyrazol-4-yl or 1-methyl-3-difluoromethylpyrazol-4-yl; $R^1$ and $R^2$ are both H.

8. A composition for controlling and protecting a plant or plant propagation material against phytopathogenic microorganisms, comprising a compound of formula (I) according to claim 1 and an inert carrier.

9. A method of controlling infestation of a plant or plant propagation material by phytopathogenic microorganisms, wherein (i) a compound of the general formula (I) according to claim 1 or (ii) a composition comprising the compound of the general formula (I) according to claim 1 as an active ingredient, is applied to the plant or plant propagation material, to a part thereof, or to a locus thereof.

10. A plant propagation material having thereon the compound of claim 1.

11. A compound of formula (I) according to claim 7, wherein said compound has a structure:

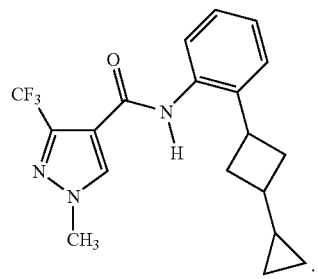

12. A composition for controlling and protecting a plant or plant propagation material against phytopathogenic microorganisms, comprising the compound according to claim 11 and an inert carrier.

13. A method of controlling infestation of a plant or plant propagation material by phytopathogenic microorganisms, wherein (i) the compound of claim 11 or (ii) a composition comprising the compound of claim 11 as an active ingredient, is applied to the plant or plant propagation material, to a part thereof, or to a locus thereof.

14. A plant propagation material having thereon the compound of claim 11.

15. A composition according to claim 8, further comprising a fertilizer.

16. A composition according to claim 11, further comprising a fertilizer.

* * * * *